Figure 1:
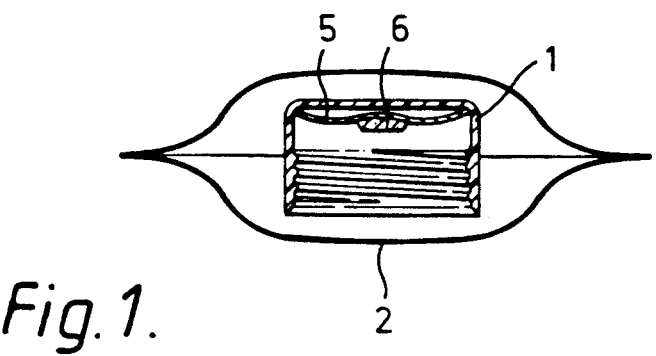

United States Patent [19]

Carr et al.

[11] Patent Number: 5,064,756

[45] Date of Patent: Nov. 12, 1991

[54] MICROBIAL SUSCEPTIBILITY ASSAY USING 7-N-(AMINOACYL)-7-AMIDO-4-METHYL-COUMARINS

[76] Inventors: Anthony H. Carr, 28 Manor Farm Way, Sharnbrook, Bedford; Robert A. Badley, 19 Well Pond Close, both of Sharnbrook, Bedford; Ian Jobling, 25 Lynford Way, Rushden, Northamptonshire; Thomas J. Sands, 52b Somerford Road, Wellingborough, Northamptonshire, all of Great Britain

[21] Appl. No.: 540,865

[22] Filed: Jun. 20, 1990

Related U.S. Application Data

[63] Continuation of Ser. No. 115,590, Oct. 26, 1987, abandoned, which is a continuation of Ser. No. 940,223, Dec. 8, 1986, abandoned, which is a continuation of Ser. No. 541,306, Oct. 12, 1983, abandoned, which is a continuation-in-part of Ser. No. 486,001, Apr. 14, 1983, abandoned.

[30] Foreign Application Priority Data

Apr. 14, 1982 [GB] United Kingdom ............... 8210825
Dec. 21, 1982 [GB] United Kingdom ............... 8236234

[51] Int. Cl.$^5$ .................... C12Q 1/18; C12Q 1/02
[52] U.S. Cl. ............................ 435/32; 435/18; 435/19; 435/29; 435/34; 436/164; 436/172; 436/800; 436/805
[58] Field of Search .................... 435/4, 18, 19, 29, 34, 435/36, 38, 32; 436/164, 172, 800, 805

[56] References Cited

U.S. PATENT DOCUMENTS

| | | | |
|---|---|---|---|
| 3,415,361 | 2/1968 | Adams et al. ............... | 436/510 |
| 3,509,026 | 4/1970 | Sanders ....................... | 435/33 |
| 4,094,647 | 6/1978 | Deutsch et al. ............. | 435/805 |
| 4,233,402 | 11/1980 | Maggio et al. ............. | 435/7 |
| 4,275,149 | 6/1981 | Litman et al. ............... | 435/7 |
| 4,374,925 | 2/1983 | Litman et al. ............... | 435/5 |
| 4,591,554 | 5/1986 | Koumura et al. ........... | 435/18 |

FOREIGN PATENT DOCUMENTS 0000063 8/1978 European Pat. Off.
5664797 6/1981 Japan.

OTHER PUBLICATIONS

Reeves et al., Antimicrobial Agents and Chemotherapy, vol. 18, No. 6, pp. 844–852 (1980).
Godsey, J. H. et al., Chemical Abstracts, vol. 94, Abstract No. 187496x (1981).
Littel et al., Applied & Environment Microbiology (1983) 45 622–627.
Smith et al., Thrombosis Research (1980) 17 393–402.
Grange et al., Journal of Clinical Pathology (1977) 13 151–153.
Kilian et al., Acta Path. Microbiol. Scand. Section B (1976) 84 245–251.
Slifkin et al., Journal of Clinical Microbiology (1983) 18 29–32:
Feng et al., Applied & Environment Microbbiology (Jun. 1982) 1320–1329.
Watson, Methods in Microbiology (1976) 9, 1.
Peterson et al., Journal of Food Science (1978) 43 1853–1856.
Bradbury, Journal of Clinical Microbiology (1977) 5 531–534.
Godsey et al., Journal of Clinical Microbiology (1981) 13 483–490.

*Primary Examiner*—Esther L. Kepplinger
*Assistant Examiner*—Toni R. Scheiner
*Attorney, Agent, or Firm*—Ostrolenk, Faber, Gerb & Soffen

[57] ABSTRACT

A method of determining the susceptibility of microorganisms to an antimicrobial substance wherein the microorganisms are cultured in the presence of the antimicrobial substance, and growth or lack of growth is assessed by detecting a fluorescent product resulting from the enzymatic hydrolysis of a fluorogenic substrate. The fluorogenic substrates include 7-N-(aminoacyl)-7-amido-4-methylcoumarin, 7-N-(alanyl)-7-amido-4-methylcoumarin, or a combination of 7-N-(alanyl)-7-amido-4-methylcoumarin and 4-methyl umbelliferyl phosphate.

10 Claims, 1 Drawing Sheet

MICROBIAL SUSCEPTIBILITY ASSAY USING 7-N-(AMINOACYL)-7-AMIDO-4-METHYLCOUMARINS

This is continuation of application Ser. No. 07/115,590, filed on Oct. 26, 1987, now abandoned, which is a continuation of application Ser. No. 06/940,223, filed on Dec. 8, 1986, now abandoned, which is a continuation of application Ser. No. 06/541,306, filed Oct. 12, 1983, now abandoned, which is a continuation-in-part of application Ser. No. 06/486,001, filed Apr. 14, 1983, now abandoned.

This invention relates to microbiological test processes and apparatus, and especially to microbial identification testing and to testing for minimum inhibitory concentrations of antibiotics in relation to clinical isolates of pathogenic microorganisms (M.I.C. testing).

It has long been the clinical laboratory practice to test microbes isolated clinically from patients and other sources for their sensitivity to antimicrobial materials and for their metabolic growth requirements. The aim of such tests is to identify the microbes and/or assess their sensitivity to antimicrobial agents in the clinical context.

Numerous methods and apparatus have been developed to aid these tests. Particularly convenient for this purpose are prepared microtitre plates provided with a series of culture wells, each containing a graduated small quantity either of an antimicrobial agent, such as for example an antibiotic, and/or a growth-promoting material, such as a vitamin, sometimes together with other ingredients for a microbial culture medium, and often in dried and otherwise stabilised form. Examples of such microtitre plates and their use are given by U.S. Pat. No. 3,713,985 (Astle), French Patent No. 1,488,866 (Sclavo), and GB Patent Specification No. 1,574,707 (Unilever). The latter specification describes the production of a particularly well-stabilised form of microtitre plate.

In use, plates of the above kinds, and other suitable devices, are inoculated with all the necessary culture materials and inoculum, and incubated until the culture result appears. Often, this culture result is seen as a "button" of growth at the bottom of a microtitre well, and typically requires at least 18 hours of incubation. (With certain fast-growing micro-organisms, this method can give "button" formation as early as 7 hours but at this stage it is generally not possible to distinguish a sensitivity test result).

It is desirable to reduce the incubation time required before a culture result can be detected. It is also desirable to render the result readable by automatic means.

Certain proposals to this end have already been made. Particular attempts are described for example in U.S. Pat. No. 4,236,211 (Pfizer) (measurement of light scatting by microorganisms in a limited number of cultures after about 5 hours, see also U.S. Pat. No. 3,832,532 and GB Patent No. 1,554,134 (Pfizer). The use of these methods calls for complex and expensive apparatus and/or extensive calculations based on the light-scattering observed. U.S. Pat. No. 4,242,337 (Bio Research) particularly describes estimation of the bacterial content of liquids by the use of fluorescence detection after exposure of bacterially contaminated specimen liquids to an enzyme-inducing medium for about 15-30 minutes, followed by reaction of the mixture with fluorescein di-beta-galactoside and fluorimetry.

U.S. Pat. No. 3,509,026 (Litton Systems Inc.) describes a culture procedure for indicating antibiotic sensitivity of microorganisms, involving the use of inert pads on a mounting strip, each containing a culture medium, antibiotic, and flavone-3-diphophate as a hydrolysable substrate to indicate bacterial growth by fluorescence. It is suggested in U.S. Pat. No. 3,509,026 that the system described will allow rapid assessment of antibiotic sensitivity, and examples are given showing the results of examination of the culture under fluorescent light after 4 hours' culture. Although some indications of antibiotic sensitivities were obtained after 4 hours' culture, there are several results denoted as unclear among the examples, and it appears to us to be at least difficult to prepare a simple and reliable system based on this technique.

More recently, T Urban and C Jarstrand have described in J Antimicrobial Chemotherapy (1981) 8, 363-369 a bacterial identification and MIC method based on commercially available Sensititre test plates, with the addition after 4 hours' culture of nitroblue tetrazolium and phenazine methosulphate to give blue formazan colour where bacterial growth has occurred. NBT and PMS are however toxic to the cultures, and it is often desired to retain the cultres after MIC or identification work for further testing.

The prior art includes a number of fluorogenic substrates for enzymes of diverse origin which are known, commercially available, and have been used in enzymological procedures. Among these are a variety of fluorogenic 4-methyl-umbelliferyl derivatives (hydrolysable to 4-methyl-umbelliferone) and derivatives of 7-amino-4-methyl-coumarin, e.g. GB Patent No. 1,547,747 and European Patent No. 0,000,063 (Ajinomoto).

By the present invention there are provided improved test materials and processes by which a reliable culture result can often by detected in respect of any of a usefully broad spectrum of micro-organisms by the use of simple procedure in as little as 4 hours after incubation, or in some cases even more quickly. These test materials and processes can in certain cases also be arranged to allow normal incubation to be continued and the ordinary culture obtained later as a confirmation if desired.

According to the present invention, there is provided an improvement in the method of carrying out a microbial culture test, in which a cultured microoganism under test is exposed to reaction with a hydrolysable fluorogenic substrate which is enzymically hydrolysable to yield a fluorescent material, and in which test any growth is assessed by fluorescence of the fluorescent material yield by hydrolysis of said fluorogenic substrate, wherein said improvement comprises using as said fluorogenic substrate a 7-(N)-(L-aminoacyl or peptidyl)-7-amido-4-methyl coumarin.

The invention can for example take the form of an improved process of determining the minimum inhibitory concentration (MIC) of an antimicrobial substance with respect to a micro-organism under test, (for example an unidentified clinical septic isolate), which process comprises (a) culturing the micro-organism in each of a series of separate culture portions of a nutrient medium, with each portion supplemented with one of a series of graded amounts (possibly including, as one of the series, a zero amount) of the antimicrobial substance of which the MIC is to be determined, (b) detecting the degree of growth of the micro-organism in the several culture portions, and (c) assessing the MIC from data representing the respective degrees of growth so detected; the improvement in the process consists essentially in the use of the fluorogenic substrates defined above, which as peptidase substrates allow detection of a surprisingly wide range of microorganisms. The inoculum concentration of the micro-organisms can be within the range of about $5 \times 10^4$ organisms per ml to $10^6$ organisms per ml, (also not necessarily above $5 \times 10^5$/ml and preferably at or below about that number); but especially when the test is to be completed in less than about 5 hours, e.g about 4–5 hours, sometimes a standard 4 hours, it can be convenient to inoculate at $5 \times 10^5$ to $4 \times 10^6$ organisms per ml, for example $2 \times 10^6$ organisms per ml. The culture portions can be exposed either during and/or after the culture period to at least one fluorogen, as mentioned above. A fluorogen is defined herein as a compound capable of being enzymically modified, e.g. by hydrolysis, to give a derivative fluorophor which has an appreciably modified or increased fluorescence. Such fluorogens can for example be conjugates of fluorophors, e.g. selected from conjugates such as phosphates, peptides, esters and possibly also glycosides, of fluorescent coumarin, and possibly also fluorescein, and indoxyl compounds and their derivatives. The exposure of the fluorogen to the cultured microorganism lasts for a sufficient time to allow any enzymic hydrolysis of the fluorogen to take place, (e.g. during the culture period itself and/or for about 30 minutes thereafter in case the fluorogen is added after the culture period). Then the fluorescence of each culture portion can be assessed, e.g. by a non-destructive instrumental fluorometric or fluoroscopic method, thereby to obtain information regarding the degree of growth in the culture, for the assessment of the MIC value after the culture period, e.g. in some preferred embodiments less than about 4–7 hours, e.g. about 3.5 to 5 hours, preferably about 4 hours. It can be useful to allow at least three generation-times for the microorganisms in the culture before assessing the results: 4 hours can be used routinely with the particular examples described hereinbelow.

This method has an advantage over current MIC assessment techniques, in that in embodiments as described below it enables a result to be obtained after a culture period of four hours, while in many cases if desired the culture can be retained, and continued by further incubation for the remainder of the conventional 16-hour or other period to enable a confirmatory result to be achieved by estimation in another way, e.g. by visual inspection of overnight cultures. Of course, such rapid results can allow rapid therapeutic decisions and can contribute to the outcome of clinical treatment of patients. The method can easily have a positive control built in, in the form of a null antibiotic well to detect lack of development of fluorescence. Generally the method can give an improvement in time needed for the test as a whole in comparison with other detection methods.

In order to obtain an effective test result, naturally the fluorogen utilised needs to be one which is hydrolysable by an enzyme produced by the micro-organism whose growth is to be detected.

Since the micro-organism can in principle be any unidentified micro-organism, there can of course possibly be difficulty in ensuring that this condition is fulfilled.

We have surprisingly found that if a fluorogen or mixture of fluorogens give an effective indication of growth for each of the following thirteen screen-test micro-organisms then it will also be suitable for use in the present rapid MIC method as applied to the overwhelming majority of clinical isolates obtained in normal microbiological practice. The thirteen screen-test micro-organisms do not themselves appear in a similarly overwhelming majority of cases, but serve as a check on the effectiveness of fluorogens in this invention. They are:

*Bacillus subtilis*
*Staphylococcus aureus*
*Streptococcus pyogenes*
*Streptococcus faecalis*
*Klebsiella edwardsii*
*Klebsiella pneumoniae*
*Proteus vulgaris*
*Proteus mirabilis*
*Escherichia coli*
*Pseudomonas aeruginosa*
*Citrobacter freundii*
*Serratia marcescens*
*Salmonella anatum.*

It is emphasised for the avoidance of doubt that these are all familiar common micro-organisms of which the wild strains are quite suitable for carrying out the assessment of fluorogens for use in the present invention and accordingly there is no need to choose particular isolated cultures or the examples stored in particular culture collections. We have verified our results in trials using multiple clinical isolates of each of multiple common species. *Staphylococcus epidermidis* can sometimes be used as a fourteenth screen test microorganism.

In accordance with this finding, one aspect of the invention therefore utilises as the fluorogen(s) a fluorogen or mixture of fluorogens which is hydrolysable to form fluorophor by a culture of each one of the above specified thirteen micro-organisms.

Specific examples of such suitable fluorogens are hydrolysable derivatives of 4-methyl-coumarin, such as (a) a mixture of 4-methylumbelliferyl phosphate and 4-methylumbelliferyl fatty acid ester such as the hexanoate, octanoate or nonanoate, or other fatty acid ester for example within the chain length range $C_6$–$C_{16}$, and (b) a mixture of 4-methylumbelliferyl ester, e.g. preferably phosphate, and a 7-(N)-(aminoacyl or peptidyl)-4-methyl-7-amino-coumarin, e.g. 7-(N)-alanyl-4-methyl-7-amino-coumarin, or the corresponding leucine derivative instead of the alanine derivative. Mixtures of other combinations of the above compounds are also suitable. Corresponding fluorogenic derivatives of other coumarins are also suitable.

These fluorogens are suitable for MIC determinations against the overwhelming majority of clinical microbial isolates. In the occasional unlucky case, it will be apparent on inspection of the cultures tht a uniform poor fluorescence yield is obtained, and thus the culture does not yield a misleading MIC value. Specific examples of fluorogens can conveniently be used for example in amounts that give the following concentrations in the culture fluid:

4-methylumbelliferyl nonanoate: 120 micromolar;
4-methylumbelliferyl phosphate: 120 micromolar; and
4-methyl-7-amino-coumarin-7-N-alanyl peptide: 100 micromolar concentration.

In general, the substrate(s) concentration is most often in the range 30 to 300 micromolar.

When 4-methylumbelliferyl nonanoate is used it can in certain embodiments preferably be added in the form of an emulsion, (e.g. formed of 6% v/v methylcellosolve containing the ester and 94% water); at or towards the end of the bacterial culture period, e.g. after 3½-4 hours, and incubated preferably about 30 minutes before assessment of the fluorescence yield and MIC: the phosphates and peptides can be present if desired throughout the culture period.

According to the invention we also provide a prepared microtitre plate having a plurality of microtitre wells containing active materials for promoting and/or inhibiting microbial growth, together with fluorogen(s) as specified herein.

In the prepared microtitre plates, the amounts and kinds of the fluorogens and other constituents are of course chosen and adjusted according to normal requirements, in the case of conventional nutrient and antibiotic ingredients, and according to the recommendations given in this specification, in the case of the fluorogens. For example, in conventional standard microtitre wells of about 0.5 ml capacity, which are suitable for use in the invention, designed to be dosed with about 50 to 100 microliters, e.g. about 0.05 ml broth in normal use, the quantity of each of the fluorogens present can very suitably be in the order of about 6 nanomoles per well.

It can be convenient to form the fluorogenic substrates, particularly the esters such as nonanoate, into an emulsion, e.g. in methoxyethanol, with a film forming stabiliser such as polyvinylalcohol, before drying down to form a stabilised film, e.g. as described in GB Patent Specification No. 1,574,707.

According to one aspect of the invention, it can be convenient to dose the fluorogens into the wells at the same time as the microbiological inoculum. In the case of many normal clinical procedures for antibiotic sensitivity testing, it is the practice to use dry prepared microtitre wells containing dried stabilised aliquots of antibiotics, e.g. as described in our earlier GB Patent Specification No. 1,574,707. Into each of these dry wells there is dispersed an aliquot of a nutrient broth containing the microbiological inoculum in suspension. The inoculum suspended in broth can be prepared as a batch, e.g. 10 ml, and dosed into wells either manually or with the use of an automatic inoculator. According to an aspect of this invention, an inoculum for dosing into a set of microtitre wells for antibiotic sensitivity testing can be prepared so as to comprise at least one or more fluorogens of the kinds described herein, at concentrations as described herein. For example, to 10 ml of broth inoculated with a clinical isolate of E.coli, of which the antibiotic sensitivity is to be determined, there can be added about 1 micromole of AAMC (4-methyl-7-aminocoumarin 7(N)-L-alanyl peptide), thus giving an AAMC concentration in the broth of about 100 micromolar concentration. For an unidentified clinical isolate, it can be especially advantageous to use a 2-component or 3-component fluorogenic substrate group, consisting of about 1 micromole of each substrate per 10 ml of inoculated broth.

If desired, the inoculum vessel, e.g. 10 ml tube, or a cap or lid or screw-top of the tube or other vessel used for preparing the inoculum, can have a dry stable preparation of the fluorogen or fluorogens in stabilised form inside it. e.g. stabilised with a thin layer of water-soluble film-forming stabiliser as described in GB Patent Specification No. 1,574,707, e.g. water-soluble polyvinyl alcohol. Another way to apply the substate mix to the inoculum is to insert a solid carrier, for example a bead, or a non-porous sheet, slip or pad, bearing a dried preparation of the substrates in appropriate predosed quantity, into the inoculum tube or other vessel used to prepare the inoculum.

It can therefore be seen that a convenient embodiment of a kit for antibiotic sensitivity testing according to this invention comprises a prepared microtitre tray with antibiotics pre-dosed in known manner in its various wells, and an inoculum preparation vessel for preparing broth-suspended inoculum for inoculation into the wells of the tray, containing in dry stabilised form one or more fluorogens as described herein, in an amount appropriate to yield detectable fluorescence after dilution in the broth, culture in the tube and hydrolysis in the event of culture growth, but distinctly different or lesser fluorescence in the event of no culture growth.

(It is understood that the fluorogenic compounds are in themselves either non-fluorescent or meta-fluorescent, i.e. fluorescent in a distinctly different way (e.g. either by colour or intensity) than the corresponding enzyme-modified products, and appropriate wavelengths of excitation and detection, in a manner well known to users of fluorometric instrumentation, are used to separate the fluorescence signal developed by the enzyme modification from any other fluorescence that may be present).

We find that this method can give good detection of an overwhelming majority of clinical isolate microorganism at 4 hours after incubation when suitable care is taken with general culture conditions and with special advantage when, in some cases an electrooptical fluorescence detector is used (e.g. a xenon lamp source such as a pulse-xenon UV source, together with a photomultiplier fluorescence detector). Suitably, such a range of detection is chosen as will allow detection of fluorophor in the range 0–14 micromolar concentration in 50–100 microliters, and preferably detects changes of concentration of 1.6 micromolar or less within this range.

The invention is illustrated by the following examples.

EXAMPLES 1 AND 2

In these examples 4-methyl-umbelliferone-phosphate (MUP) (Example 1) and 4-methyl-umbelliferone nonanoate (MUN) (Example 2) are exposed to a culture of bacteria to give an indication of the amount of bacterial growth by the extent of their conversion to 4-methyl-umbelliferone (4MU), measured fluorometrically.

Microtitre wells were dosed (Example 1) with 0.05 ml of a medium containing casein hydrolysate (1.75% w/w); Difco (TM) brain heart infusion (0.45%), $CaCl_2$ (0.017%), $MgCl_2$ (0.025%), and also (in the case of MUP) containing 120 micromolar MUP. In the case of Example 2, MUN was reserved until a later stage.

Each combination of materials was tested in the presence and absence of inoculum and in the presence and absence of various concentrations of each of a number of commonly used therapeutic antibiotics.

To make the test inocula, each of fourteen test organisms as specified above was grown overnight in culture in a medium similar to that described above except that it lacked the fluorogenic substrate. These cultures were used as a test source of inocula for the dosed microtitre wells each containing 50 microliters at a concentration of $10^5$ cells per ml (final count in the inoculated wells).

Incubation of the plates was carried out over four hours at 37° C. In the case of the MUN plates, after this period to each relevant well to be dosed there was added 18 microliter of an emulsion of MUN in methoxyethanol and water (made at the rate of 15.82 mg MUN dissolved in 1.5 ml methoxyethanol and emulsified with pure water to 25 ml volume, giving 2 mM substrate in the emulsion). The dosed wells where then incubated at 37° C. for 30 minutes.

The fluorometric detection system used consisted of a pulsed-light xenon source and fluorimeter, (in this case a xenon lamp system 3021 and pulsed-light photometer system 3010 from Chelsea Instruments Limited, London) operated with a Schott 2-branch fibre-optic UV light guide (Schott Glass Limited) with 500 mm light guide length and 4 mm diameter branch optical fibre bundle dimeters. The excitation wavelength used was 363 nm. The emission (detector) wavelength used was 450 nm. This combination of wavelengths is found to offer the best compromise with these substrates between absorbance from the 4-MU product and competing absorbance from MUP and MUN.

An alternative optical system used consisted of a Perkin-Elmer 1000 fluorimeter set with 363 nm excitation wavelength, 450 nm emission wavelength, narrow slit width, energy level 400, scale expansion 1, 0.5 cm light path, and temperature 37° C.

The pulsed light xenon system was advantageous in that it allowed the measurements to be taken while the cultures remained in their culture wells.

The MIC value in the antibiotic tests was taken as that least concentration of antibiotic in the well in which the fluorescence level detected after culture was no more than twice the background level.

In the tests described above it was found that the use of the indicated amount of MUP allowed detection of growth and antibiotic inhibition after 4 hours' growth of *S aureus, Strep. pyogenes, Kl.edwardsii, Kl.pneumoniae, Pr.mirabilis, E.coli, Citr.freundii, Serr.marcescens,* and *Salm.anatum*.

By the use of MUN alone it was possible to detect growth and antibiotic inhibition of *B.subtilis, Staph.aureus, Staph.epidermidis, Strep.pyogenes, Kl.pneumoniae, Ps.aeruginosa, Serr.marcescens* and *Salm.anatum*.

The use of MUN and MUP together was effected in a supplementary Example (1+2) by treating culture wells which had been based on MUP-containing medium, as in Example 1, with MUN in the manner described in Example 2. Using this combination it was possible to detect growth and antibiotic inhibition of all fifteen above-described test microorganisms.

EXAMPLE 3

In a similar manner to that described for Example 1, the peptide L-alanyl-7-amido-4-methylcoumarin (AAMC) was used as a fluorogenic substrate, and gave the ability to detect growth and inhibition of all fifteen of the above-specified test microorganism after a culture period of 4 hours. It was found advantageous in some cases, e.g. to give a more intense result with *B.subtilis* and *S.aureus* and some others, to use AAMC in combination with MUN.

EXAMPLE 4

This example illustrates a preferred method of applying fluorogenic materials to the improvement of microbial MIC determinations, involving the application of fluorogenic enzyme substrates to the broth suspensions of the microbial inocula. The materials used in this example included a standard prepared plate for MIC determinations ('Sensititre' (Trade Mark) from Seward Laboratory in UK, Gibco Diagnostics in USA), including $12 \times 8$ microtitre wells each to contain 0.05 ml broth suspension.

A broth suspension of microorganisms was prepared by the use of a prepared sterile inoculum tube of standard form and 10 ml working capacity, with a plastic screw-top, filled with 10 ml of the nutrient medium specified in Example 1 and sterilised. A suspension of the microorganism was made to a final density of $2.5 \times 10^5$ organisms/ml as judged by optical comparison of the turbidity of a 10–40-fold concentrate (e.g. $10^7$/ml)using a MacFarlan standard suspension of $BaSO_4$ and/or the experienced eye of a microbiological technician. The broth was prewarmed in the inoculator tube to 37° C. before dispersion of the microbial inoculum therein, so that thermal shock was avoided as far as possible.

The fluorogenic substrates 4-methyl-umbelliferyl phosphate, (MUP), 4-methyl-umbelliferyl nonanoate (MUN), and L-alanyl-7-amino-4-methylcoumarin (AAMC) were introduced into the broth suspension of the microoganism in the following manner.

Figure 2:
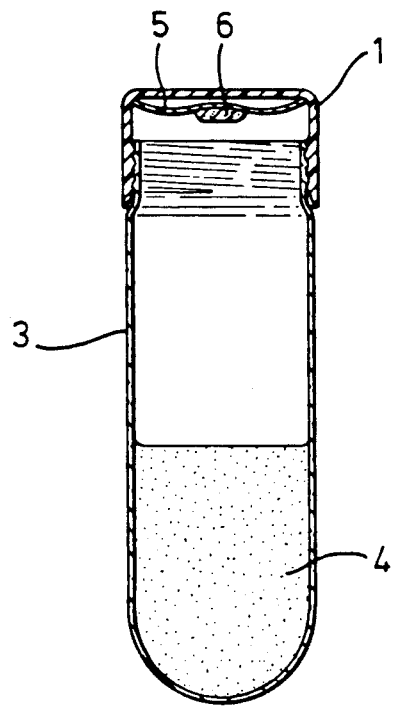

A second screw-cap for the sterile broth tube, as illustrated in FIGS. 1 and 2 of the accompanying drawings, had previously been predosed with a preparation of the substrates an stored in dry form in a moisture-impermeable wrapping until required for use. The substrate preparation consisted of the following compositions mixed by adding them together sequentially in the following order, (a) 307.3 mg MUP dissolved in 5 ml 0.5% aqueous polyvinyl alcohol (water soluble, Sigma type P-8136 from Sigma Chemical Company); to which is then added (b) 246.2 mg AAMC dissolved in 10 ml 2-methoxyethanol, to which is finally added (c) 380.0 mg MUN dissolved in 10 ml 2-methoxyethanol.

This mixture was sufficient to prepare 1000 predosed screwcaps of fluorogenic substrates. As shown diagrammatically in section in FIGS. 1 and 2, a standard inoculator tube cap 1 was used, which was sealed in an impermeable packaging 2. When required for use it was removed from packaging 2 and used to cap a standard (10 ml) inoculator tube 3 containing a nutrient suspension 4 of microorganisms. The tube cap 1 consisted of a plastics cap body containing a water- and solvent-impermeable sealing wad 5. A small depression was made in the centre of each wad (if needed) and a drop of 0.025 ml of the prepared substrate mixture dosed into the depression so formed in the wad of each cap. The methods and conditions adopted in connexion with the dosing and drying are those which have become conventional in the preparation of "Sensititre" products and are in detail substantially as described in GB Specification Nos. 1,574,707, 1,520,745 and 1,508,747. The result was a dried spot 6 (FIGS. 1 and 2) in each cap containing the mixture of substrates. Each cap then contains 1.2 micromoles MUP, 1 micromole MUN and 1.2 micromoles AAMC. When the warm (37° C.) microbial broth suspension had been prepared in a standard inoculator tube, the plain screw-cap of the tube (not shown in the drawings) was then exchanged for one of the prepared screw-caps 1 described above, as indicated in FIG. 2, and shaken up for about 30 seconds to dissolve and/or disperse the fluorogenic substrates located on the cap-wad.

Then the prepared broth suspension, in this way loaded with the fluorogenic substrates, was dosed into the prepared "Sensititre" plate in the normal manner, and incubated in the normal manner except that the incubation period was 4 hours instead of the normal 18–20 hours.

At the end of the 4 hours incubation period, the fluorescence of each well was read by means of a fluorescence detector arranged for adequate sensitivity, back-off and overload performance to give usable signal read-out from a 50 microliter sample containing free fluorophor concentrations (reckoned as 7-amino-4-methylcoumarin) in the range 0–3 micromolar and up to 14 micromolar concentration. A concentration of 3 micromolar 7-AMC correspond to the order of magnitude of degrees of fluorescence typically found after 4 hours' culture of inocula prepared according to the invention.

An important advantage of the procedure was that (wherever desired) the fluorescent plates could be cultured on overnight in the normal manner to obtain a conventional culture result. This can provide the clinical user with reassurance about the correctness of the result obtained after 4 hours.

An important methodological point in the use and application of this system is the criterion for judging the presence or absence of microbial growth and the correlation of the results with the standard "Sensititre" method and other (manual) minimum inhibitory concentration tests which have been shown to correlate well with each other. (See D S Reeves et al., *Antimicrobial Agents and Chemotherapy*, December 1980, 18 (6), pp 844–852).

In the present example, a negative control fluorescence level is taken from the fluorescence yield of control wells which are complete and have been subjected to the entire procedure except for the absence of microorganisms. (Alternatively or additionally, it could be taken from the fluorescence yields of wells containing such high concentrations of antibiotic that the microorganisms dosed into them have not grown).

A single MIC determination is based on the antibiotic concentration in the last well (in a series showing decreasing concentrations of a single antibiotic) before the first well of the series in which definite growth is detected.

In this example, "definite growth" is indicated by an increase of fluoresence yield compared to the negative control after 4 hours of incubation, but is not taken as indicated unless (i) the fluoresence yield from the well is at a level greater than the sum of negative control level and one third of the range between the negative control well and maximum yield for the organism in question (zero antibiotic); and (ii) the fluorescence yield from the well is equivalent to more than 1.6 micromolar (as concentration of 4-methylumbelliferone) fluorophor difference between the well and the average of the wells tested so far in the current row or set, i.e. the current single antibiotic dilution series, and (iii) the fluorescence yield from the well is greater than the negative control level by more than 1.96 times the standard deviation of the average of the wells tested so far.

For the evaluation of any one row or column of wells, with a given antibiotic dilution series the background level is first taken as the fluorescence yield of the first well, and thereafter as the running mean of levels of wells already examined and showing no definite growth. The standard deviation is taken as 2.5% when evaluating the second well and is then calculated from the levels of the wells so far examined in the row and showing no growth.

It has to be emphasised that this is the method of calculation we have arrived at to give the best available correlation with existing MIC methods, and the method of the present invention does indeed correlate well with these, provided tht induced-resistance phenomena are allowed for (see below).

However, this method of calculation deliberately ignores occasional low levels of growth occuring in wells where the antibiotic is present at a level currently accepted as being the MIC itself. The existing standard methods, in fact, are not able to detect such low levels of growth even after 18–20 hours incubation. We consider that in such cases the conventional estimates of the MIC are on the low side, and that an appropriate level for therapeutic decision lies rather at the higher levels which are capable of being indicated by the method of this invention using modified rules of calulation which do not ignore the low levels of microbial growth sometimes obtained near the currently-accepted MIC level.

Where this criterion of interpretation of the test results is chosen, condition (i) for the indication of "definite growth" may be ignored or the threshold level reduced to one sixth or one tenth of the range between negative-control and maximum-growth fluorescence yields.

It is believed that when used in this way, the method of the invention not only gives a rapid and convenient test result but also an advance in sensitivity and discrimination, compared with the existing methods.

One further factor in using methods of the present invention and interpreting them needs to be mentioned, and that is the phenomenon of induced resistance of the antibiotics under test.

With some microbes, especially with *Staphylococcus aureus*, a resistance to antibiotic, especially beta-lactam antibiotics such as those of the penicillin and cephalosporin series, can often show itself only after overnight culture in the presence of the antibiotic. Thus 4-hour culture results, by whatever method evaluated, can show inhibition by antibiotic while 18-hour culture results show subsequent recovery and growth after induction of the resistance.

Where effects of this kind are suspected then either a 4-hour culture result has intrinsically to be treated with caution and subject to confirmation, or steps can be taken to avoid an appearance of antibiotic susceptibility where resistance would develop in the longer term. Thus, for example, the preincubation culture which is carried out in order to obtain the inoculum suspension of a possiby beta-lactam-antibiotic resistant strain used for the MIC test, can be carried out in the presence of a non-lethal amount of a beta-lactam antibiotic such as penicillin G or methicillin, such an amount being used as will induce the formation of the beta-lactamase enzyme responsible for the resistance, in a manner which is known per se. Suggested concentrations for this condition are for example of the order of 0.25 microgram per ml methicillin inducer.

A number of alternative fluorogenic substrates can be used in modifications of the system described above, namely for example peptides and esters (in themselves known materials) of umbelliferone, 4-methylumbelliferone, 3-carboxy-7-hydroxycoumarin, 3-carboxamido-7-hydroxycoumarin, 3-phenyl-7-hydroxycourmarin, 3-acteyl-7-hydroxycoumarin, 3-carboxyethyl-7-hydroxycoumarin, 3-cyano-7-hydroxycoumarin, 7-amino-4-methylcoumarin, 7-amino-4-trifluoromethylcoumarin, 2-naphthylamine, 4-methoxy-beta-naphthlamine, naphthol-AS (3-hydroxy-2-naphthoic acid anilide), indoxyl and 1-(alpha) - and 2-(beta)-naphthol derivatives including N-methyl indoxyl acetate and indoxyl acetate, resorufin, 1-methyl-7-hydroxyquinolinium iodide, and 6-amino-quinoline.

EXAMPLE 5

This example shows the preparation of microtitre wells containing stabilised fluorogenic substrates, suitable for carrying out several embodiments of the invention. Directions are as follows:

Dissolve 307 mg 4-methyl umbelliferyl phospate (Koch-Light) in 5 ml distilled water by agitating in a 70° C. water bath and then filter-sterilise. Mix with 5 ml 5% w/v polyvinyl alcohol (Sigma type II No. P8136) which has been autoclaved at 121° C. for 15 minutes before allowing to cool. Dissolve 660 mg 7-L-alanyl-7-amido-4-methyl-coumarin, commercially obtained in the form of its trifluoroacetate, (Cambridge Research Biochemicals) in 20 ml 2-methyloxyethanol. Dissolve 304 mg 4-methyl umbelliferyl nonanoate (Koch-Light) in 20 ml 2-methoxyethanol.

Mix the two 2-methoxyethanol solutions together, followed by the PVA solution. Dose 100 microliters into each microtitre well and dry at 55° C., 20 Torr for 1 hour. Pack in an air and light tight container with a desiccant until required for use. Each microtitre well thus prepared is ready for the inoculation with standard quantities of microorganism suspension in nutrient broth.

It is convenient, when required, to include in the methoxyethanol/polyvinylalcohol mixtures appropriate quantities of any standard growth-inhibiting or growth-promoting substances needed for the cultures to be carried out in the microtitre wells. Alternatively, these can be introduced in separate dosing and drying operations or as liquid additives prior to inoculation.

Remaining details for carrying out cultures are standard, and for reading the fluorescent results are as described earlier in this specification.

EXAMPLE 6

This example shows the preparation of dosed paper strips for addition to a microbial inoculum suspension in culture medium for inoculating culture test plates, and is an alternative to the dried-down cap preparation described in Example 3. Directions are as follows:

Dissolve 153.5 mg 4-methyl umbelliferyl phosphate (Koch-Light) in 2.5 ml distilled water by agitating in a 70° C. water bath and then filter-sterilise. Mix with 2.5 ml 30% w/v polyvinyl alcohol (Sigma type II No. P8136) which has been autoclaved at 121° C. for 15 minutes before allowing to cool. Dissolve 330 mg 7-L-alanyl-7-amido-4-methyl-coumarin, commerically obtained in the form of its trifluoroacetate, (Cambridge Research Biochemicals) in 10 ml 2-methoxyethanol.

Mix the two 2-methoxyethanol solutions together followed by the PVA solution. Dose 100 microliter into non-porous strips 9 mm×14.7 mm as used for drying antibiotics and dry at 55° C., 20 Torr for 1 hour. Pack in an air and light tight container with a desiccant until required for use.

In conclusion, it can be seen that the invention provides a wide variety of improved antibiotic sensitivity tests and corresponding culture methods and pre-dosed test plates, and microtitre wells, broth containers, closures and inserts adapted thereto. The skilled reader will be able to select those which suit his particular needs, for example, a procedure using AAMC can conveniently be used when it is desired to carry out tests for *E.coli* and substantially all other gram-negative enteric organisms, and a procedure using one of the combinations of fluorogenic substrates is a useful example for screening the sensitivity of isolates drawn from a large and unidentified wild population. It can be convenient in certain instances to carry out a preliminary screening of an unidentified microorganism in contact with the fluorogenic substrate or combination chosen, to verify that its presence can result in the development of satisfactory levels of fluorescence.

The features and characteristics presented in this specification and accompanying claims can be carried out, used and performed in all combinations and not merely in those specifically exemplified herein.

We claim:

1. In a method of determining the susceptibility of microorganisms to an antimicrobial substance, comprising culturing the microorganisms in the presence of an antimicrobial substance, contacting the microorganisms with a fluorogenic substrate which is enzymatically hydrolyzable to yield a fluorescent product, and determining growth by measuring the fluorescent product yielded by the hydrolysis of the fluorescent substrate, wherein the improvement comprises using as said fluorogenic substrate a 7-N-(aminoacyl)-7-amido-4-methylcoumarin and exposing the microorganisms to the fluorescent substrate throughout culturing.

2. The method of claim 1 wherein the microorganisms are initially present at a concentration of $5 \times 10^4$ to $4 \times 10^6$ microorganisms per ml.

3. The method of claim 1 wherein the microorganisms are cultured for a period of 3.5 to 7 hours.

4. The method of claim 1 further comprising culturing the microorganisms in the presence of the fluorogenic substrate in a plurality of culture vessels, wherein the culture vessels contain serial dilutions of the antimicrobial substance and wherein growth or lack of growth of the microorganisms is used to determine the minimum inhibitory concentration of the antimicrobial substance.

5. In a method of determining the susceptibility of microorganisms to an antimicrobial substance, comprising culturing the microorganisms in the presence of an antimicrobial substance, contacting the microorganisms with a fluorogenic substrate which is enzymatically hydrolyzable to yield a fluorescent product, and determining growth by measuring the fluorescent product yielded by the hydrolysis of the fluorescent substrate, wherein the improvement comprises using as said fluorogenic substrate a 7-N-(alanyl)-7-amido-4-methyl-coumarin.

6. The method of claim 5 further comprising exposing the microorganisms to the fluorescent substrate throughout culturing.

7. The method of claim 6 wherein the microorganisms are initially present at a concentration of $5 \times 10^4$ to $4 \times 10^6$ microorganisms per ml.

8. In a method of determining the susceptibility of microorganisms to an antimicrobial substance, comprising culturing the microorganisms in the presence of an antimicrobial substance, contacting the microorganisms with a fluorogenic substrate which is enzymatically hydrolyzable to yield a fluorescent product, and determining growth by measuring the fluorescent product yielded by the hydrolysis of the fluorescent substrate, wherein the improvement comprises using as said fluorogenic substrate a combination of 7-N-(aminoacyl)-7-amido-4-methylcoumarin and 4-methyl umbelliferyl phosphate.

9. The method of claim 8 further comprising exposing the microorganisms to the fluorescent substrate throughout culturing.

10. The method of claim 9 wherein the microorganisms are initially present at a concentration of $5 \times 10^4$ to $4 \times 10^6$ microorganisms per ml.

* * * * *